United States Patent
Cok et al.

(10) Patent No.: US 9,416,281 B1
(45) Date of Patent: *Aug. 16, 2016

(54) MAKING IMPRINTED MULTI-LAYER BIOCIDAL PARTICLE STRUCTURE

(71) Applicant: Eastman Kodak Company, Rochester, NY (US)

(72) Inventors: Ronald Steven Cok, Rochester, NY (US); Mitchell Stewart Burberry, Webster, NY (US)

(73) Assignee: EASTMAN KODAK COMPANY, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/607,104

(22) Filed: Jan. 28, 2015

(51) Int. Cl.
*B29C 59/00* (2006.01)
*B44C 1/22* (2006.01)
*C09D 5/14* (2006.01)
*B29C 59/02* (2006.01)
*B29K 105/24* (2006.01)
*B29K 105/00* (2006.01)

(52) U.S. Cl.
CPC ............ *C09D 5/14* (2013.01); *B29C 59/026* (2013.01); *B29K 2105/0011* (2013.01); *B29K 2105/24* (2013.01)

(58) Field of Classification Search
None
See application file for complete search history.

(56) References Cited

U.S. PATENT DOCUMENTS

| | | | |
|---|---|---|---|
| 6,955,845 B1 * | 10/2005 | Poole et al. | 428/76 |
| 7,143,709 B2 | 12/2006 | Brennan et al. | |
| 7,579,396 B2 | 8/2009 | Blanton et al. | |
| 7,820,284 B2 | 10/2010 | Terry | |
| 9,186,698 B1 * | 11/2015 | Wang et al. | |
| 2008/0242794 A1 | 10/2008 | Sandford et al. | |
| 2010/0034900 A1 | 2/2010 | Temchenko et al. | |
| 2010/0093851 A1 | 4/2010 | Blanton et al. | |
| 2010/0167181 A1 * | 7/2010 | Kim | 430/5 |
| 2012/0164433 A1 * | 6/2012 | Advincula | 428/327 |
| 2014/0193612 A1 * | 7/2014 | Yu et al. | 428/143 |

FOREIGN PATENT DOCUMENTS

CN 102063951 7/2013

* cited by examiner

*Primary Examiner* — Shamim Ahmed
(74) *Attorney, Agent, or Firm* — Raymond L. Owens; William R. Zimmerli

(57) ABSTRACT

A method of making a multi-layer biocidal structure includes providing a support and locating a first curable layer on the support, the first curable layer including dispersed multiple biocidal particles. A second curable layer is located on the first curable layer; the multiple biocidal particles are dispersed within only the first curable layer. The first curable layer and the second curable layer are imprinted in a single step with an imprinting stamp having a structure with a depth greater than the thickness of the second curable layer. The first curable layer and the second curable layer are cured in a single step to form a first cured layer and a second cured layer. The imprinting stamp is removed.

14 Claims, 10 Drawing Sheets

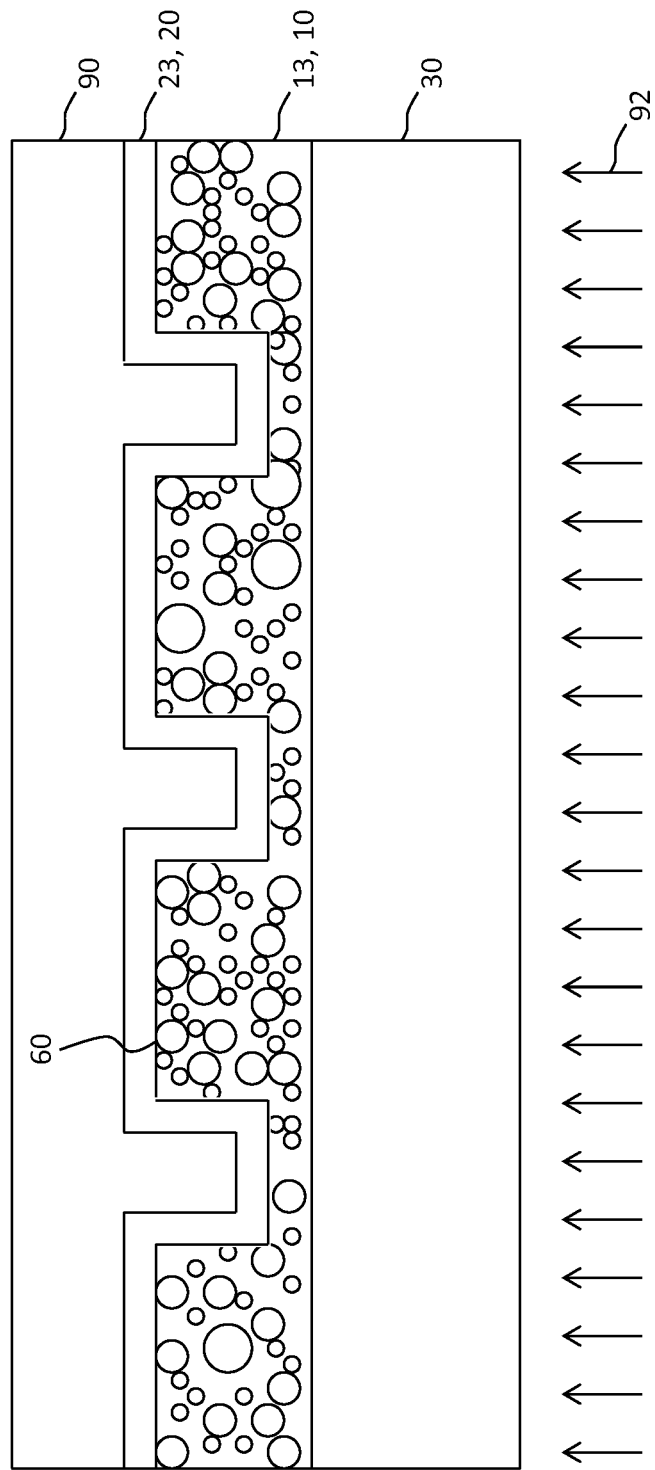

MAKING IMPRINTED MULTI-LAYER BIOCIDAL PARTICLE STRUCTURE

CROSS REFERENCE TO RELATED APPLICATIONS

Reference is made to commonly-assigned co-pending U.S. patent application Ser. No. 14/607,100, filed Jan. 28, 2015, entitled Imprinted Multi-layer Biocidal Particle Structure, by Burberry et al, to commonly-assigned co-pending U.S. patent application Ser. No. 14/607,109, filed Jan. 28, 2015, entitled Using Imprinted Multi-layer Structure, by Cok et al, and to commonly-assigned co-pending U.S. patent application Ser. No. 14/526,619 filed Oct. 29, 2014, entitled Making Imprinted Multi-layer Biocidal Particle Structure, by Cok et al.

FIELD OF THE INVENTION

The present invention relates to biocidal layers having antimicrobial efficacy on a surface.

BACKGROUND OF THE INVENTION

Widespread attention has been focused in recent years on the consequences of bacterial and fungal contamination contracted by contact with common surfaces and objects. Some noteworthy examples include the sometimes fatal outcome from food poisoning due to the presence of particular strains of *Escherichia coli* in undercooked beef; *Salmonella* contamination in undercooked and unwashed poultry food products; as well as illnesses and skin irritations due to *Staphylococcus aureus* and other micro-organisms. Anthrax is an acute infectious disease caused by the spore-forming bacterium bacillus anthracis. Allergic reactions to molds and yeasts are a major concern to many consumers and insurance companies alike. In addition, significant fear has arisen in regard to the development of antibiotic-resistant strains of bacteria, such as methicillin-resistant *Staphylococcus aureus* (MRSA) and vancomycin-resistant *Enterococcus* (VRE). The U.S. Centers for Disease Control and Prevention estimates that 10% of patients contract additional diseases during their hospital stay and that the total deaths resulting from these nosocomially-contracted illnesses exceeds those suffered from vehicular traffic accidents and homicides.

In response to these concerns, manufacturers have begun incorporating antimicrobial agents into materials used to produce objects for commercial, institutional, residential, and personal use. Noble metal ions such as silver and gold ions are known for their antimicrobial properties and have been used in medical care for many years to prevent and treat infection. In recent years, this technology has been applied to consumer products to prevent the transmission of infectious disease and to kill harmful bacteria such as *Staphylococcus aureus* and *Salmonella*.

In common practice, noble metals, metal ions, metal salts, or compounds containing metal ions having antimicrobial properties can be applied to surfaces to impart an antimicrobial property to the surface. If, or when, the surface is inoculated with harmful microbes, the antimicrobial metal ions or metal complexes, if present in effective concentrations, will slow or even prevent altogether the growth of those microbes. Recently, silver sulfate, $Ag_2SO_4$, described in U.S. Pat. No. 7,579,396, U.S. Patent Application Publication 2008/0242794, U.S. Patent Application Publication 2009/0291147, U.S. Patent Application Publication 2010/0093851, and U.S. Patent Application Publication 2010/0160486 has been shown to provide efficacious antimicrobial protection in polymer composites. The United States Environmental Protection Agency (EPA) evaluated silver sulfate as a biocide and registered its use as part of EPA Reg. No, 59441-8 EPA EST. NO. 59441-NY-001. In granting that registration, the EPA determined that silver sulfate was safe and effective in providing antibacterial and antifungal protection. Antimicrobial activity is not limited to noble metals but is also observed in other metals such as copper and organic materials such as triclosan, and some polymeric materials.

It is important that the antimicrobial active element, molecule, or compound be present on the surface of the article at a concentration sufficient to inhibit microbial growth. This concentration, for a particular antimicrobial agent and bacterium, is often referred to as the minimum inhibitory concentration (MIC). It is also important that the antimicrobial agent be present on the surface of the article at a concentration significantly below that which can be harmful to the user of the article. This prevents harmful side effects of the article and decreases the risk to the user, while providing the benefit of reducing microbial contamination. There is a problem in that the rate of release of antimicrobial ions from antimicrobial films can be too facile, such that the antimicrobial article can quickly be depleted of antimicrobial active materials and become inert or non-functional. Depletion results from rapid diffusion of the active materials into the biological environment with which they are in contact, for example, water soluble biocides exposed to aqueous or humid environments. It is desirable that the rate of release of the antimicrobial ions or molecules be controlled such that the concentration of antimicrobials remains above the MIC. The concentration should remain there over the duration of use of the antimicrobial article. The desired rate of exchange of the antimicrobial can depend upon a number of factors including the identity of the antimicrobial metal ion, the specific microbe to be targeted, and the intended use and duration of use of the antimicrobial article.

Antimicrobial coatings are known in the prior art, for example as described in U.S. Patent Application Publication 2010/0034900. This disclosure teaches a method of coating a substrate with biocide particles dispersed into a coating so that the particles are in contact with the environment. In other designs, for example as taught in U.S. Pat. No. 7,820,284, a polymeric overcoat is applied over a base coat including anti-microbial particles. The overcoat is permeable or semi-permeable to the agents released from the anti-microbial particles. Non-planar coatings are also known to provide surface topographies for non-toxic bio-adhesion control, for example as disclosed in U.S. Pat. No. 7,143,709.

Imprinting methods useful for forming surface topographies are taught in CN102063951. As discussed in CN102063951, a pattern of micro-channels are formed in a substrate using an embossing technique. Embossing methods are generally known in the prior art and typically include coating a curable liquid, such as a polymer, onto a rigid substrate. A pattern of micro-channels is embossed (impressed or imprinted) onto the polymer layer by a master having an inverted pattern of structures formed on its surface. The polymer is then cured.

Fabrics or materials incorporating biocidal elements are known in the art and commercially available. U.S. Pat. No. 5,662,991 describes a biocidal fabric with a pattern of biocidal beads. U.S. Pat. No. 5,980,620 discloses a means of inhibiting bacterial growth on a coated substrate comprising a substantially dry powder coating containing a biocide. U.S. Pat. No. 6,437,021 teaches a water-insoluble polymeric support containing a biocide. Methods for depositing thin silver-comprising films on non-conducting substrates are taught in U.S. Patent Application Publication No. 2014/0170298.

SUMMARY OF THE INVENTION

It is important that any anti-microbial surface coating or material be efficacious when it is provided in a desired environment, that it continues to be efficacious over a desired lifetime, and that the anti-microbial surface coating or material be robust in the presence of environmental contaminants, such as gases or liquids. In particular, it is useful to clean the anti-microbial surface coating or material, for example with water or other cleaners.

The efficacy of antimicrobial coatings and materials depend at least in part on their structure, surface area, and the rate at which and duration for which the antimicrobial material is exposed to microbes. There is a need, therefore, for antimicrobial coatings with improved efficacy, environmental robustness, and reduced costs.

In accordance with the present invention, a method of making a multi-layer biocidal structure includes:
  providing a support;
  locating a first curable layer on the support, the first curable layer including dispersed multiple biocidal particles;
  locating a second curable layer on the first curable layer, wherein multiple biocidal particles are dispersed within only the first curable layer;
  imprinting the first curable layer and the second curable layer in a single step with an imprinting stamp having a structure with a depth greater than the thickness of the second curable layer;
  curing the first curable layer and the second curable layer in a single step to form a first cured layer and a second cured layer; and
  removing the imprinting stamp.

The present invention provides a biocidal multi-layer structure that provides improved antimicrobial properties with thinner layers having increased surface area made in a cost-efficient process. The biocidal multi-layer structure is robust in the presence of environmental contaminants and cleaning agents.

BRIEF DESCRIPTION OF THE DRAWINGS

The above and other features and advantages of the present invention will become more apparent when taken in conjunction with the following description and drawings wherein identical reference numerals have been used to designate identical features that are common to the figures, and wherein:

FIGS. 2A-2G are cross sections of sequential construction steps useful in a method of the present invention;

The Figures are not drawn to scale since the variation in size of various elements in the Figures is too great to permit depiction to scale.

DETAILED DESCRIPTION OF THE INVENTION

The present invention provides a multi-layer structure useful in forming an antimicrobial or biocidal article on a support. Multi-layer structures of the present invention provide improved antimicrobial properties and usability made in a cost-efficient process. In useful methods of the present invention, multiple uncured coatings are formed on a support, imprinted together, and then cured together. A thin top layer can control the rate at which antimicrobial elements are exposed to the environment and also provide environmental protection to the antimicrobial materials, for example provide protection from cleaning agents. The imprinted layers provide a greater surface area for the antimicrobial materials and a topographical structure that inhibits the growth and reproduction of microbes. Coating and imprinting processes provide a cost-efficient manufacturing method.

Figure 1:
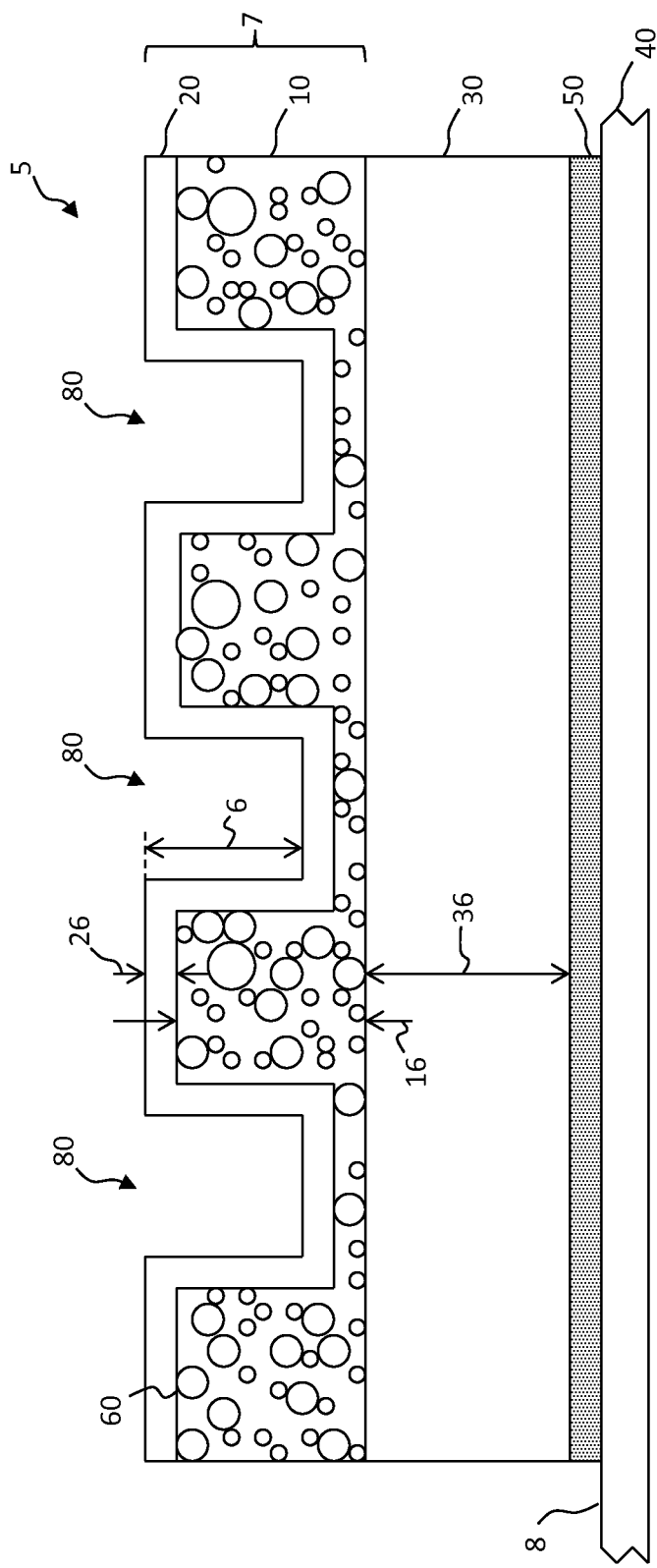
FIG. 1 is a cross section of a multi-layer structure illustrating an embodiment of the present invention.

Referring to FIG. 1, in an embodiment of the present invention, an imprinted multi-layer structure 5 includes a support 30 having a support thickness 36. A bi-layer 7 having a topographical structure is located on or over the support 30. The bi-layer 7 includes a first cured layer 10 on or over the support 30 and a second layer 20 on a side of the first cured layer 10 opposite the support 30. In an embodiment, the second layer 20 is a second cured layer 20. The first cured layer 10 has a first-layer thickness 16 and the second cured layer 20 has a second-layer thickness 26. Multiple biocidal particles 60 are located in the first layer 10. Indentations 80 with a depth 6 are located in the first and second cured layers 10, 20 to form a topographical structure in the bi-layer 7. At least one depth 6 of the topographical structure is greater than the second-layer thickness 26. By providing a topographical structure depth 6 that is greater than the second-layer thickness 26, embodiments of the present invention provide both a topographical structure that inhibits the growth and reproduction of microbes and increased surface area having a reduced thickness through which biocidal agents (e.g. biocidal particles 60) are exposed to the environment. In some embodiments, the depth 6 is between 0.5 microns and 50 microns or between 0.5 microns and 10 microns, or between 0.5 microns and 5 microns, or 0.5 microns to 2 microns.

In a useful arrangement, the support 30 is adhered with an adhesive layer 50 to a surface 8 of a structure 40. In embodiments, the adhesive is a binder or primer. Alternatively, or in addition, the adhesive layer 50, binder, or primer can form the surface 8 on the support 30 on which the first cured layer 10 is readily coated, for example by controlling the surface energy of the support surface or the first cured layer 10. In another embodiment, an adhesion-promoting layer is located between the first and second curable layers 10, 20 (not shown) to adhere the first cured layer 10 and the second cured layer 20 together and enable the second cured layer 20 to be coated over the first cured layer 10 before the first cured layer 10 and the second cured layer 20 are imprinted to form the indentations 80 of the bi-layer 7 and the imprinted multi-layer structure 5.

In an embodiment of the present invention, the biocidal particles 60 are located only in the first cured layer 10. Thus, the second cured layer 20 provides environmental protection to the biocidal particles 60 and protects the biocidal particles 60 from environmental contaminants, such as dirt, moisture, gases, and liquids including cleaning agents. In another embodiment, the first cured layer 10 includes a first material and the second cured layer 20 includes a second material that is different from the first material. Alternatively, the first cured layer 10 and the second cured layer 20 include one or more common materials.

Coating or other deposition methods for forming multiple layers on a substrate are known in the art, such as curtain or hopper coating or laminating, as are imprinting and curing methods useful for forming the indentations 80 in the first and second cured layers 10, 20. Curable materials, for example heat or radiation sensitive resins are also known as are supports such as glass or plastic, adhesives, and surfaces such as walls, tables, cylinders, handles and the like.

In an embodiment, the second cured layer 20 is thinner than the first cured layer 10. As shown in FIG. 1, the first cured layer 10 has portions having the first-layer thickness 16 that are thicker than the second-layer thickness 26. A thin second cured layer 20 can provide protection from environmental contaminants while permitting biocidal agents to effectively enter the environment. In an alternative embodiment, the second-layer thickness 26 is greater than the first-layer thickness 16.

As used herein, a structured layer is a layer that is not smooth or not planar on a microscopic scale corresponding to the magnitude of the indentations 80. For example if the support 30 is planar, a structured layer formed on the support 30 according to the present invention is flat but non-planar and is not smooth. If the support 30 is not planar but is smooth, for example having a surface that is curved in one or more dimensions (such as a spherical section), a structured layer formed on the support 30 according to the present invention is not flat and is not smooth. Whether or not the support 30 is planar, the structured layer can include indentations 80, channels, pits, holes, extended portions, mesas or other physical elements or structures. In one embodiment, the surface is rough. The depth 6 of the bi-layer 7 is the distance from an exposed surface of the portion of the bi-layer 7 furthest from the support 30 to an exposed surface of the portion of the bi-layer 7 that is closest to the support 30 in a direction that is orthogonal to a surface of the support 30.

In an embodiment, the first cured layer 10 is located on or over the support 30. The support 30 is any layer that is capable of supporting the first and second cured layers 10, 20 and in different embodiments is rigid, flexible, or transparent and, for example is a substrate made of glass, plastic, paper, or vinyl or combinations of such materials or other materials. In an embodiment, the first cured layer 10 is cross linked to the second cured layer 20 to provide rigidity and improved strength for the layers and to prevent delamination of the first cured layer 10 form the second cured layer 20.

In a useful arrangement, the support 30 is adhered, for example with an adhesive layer 50 such as a pressure-sensitive adhesive or glue such as wall-paper glue, to the surface 8 of the structure 40. The surface 8 is any surface 8, planar or non-planar that is desired to resist the growth of biologically undesirable organisms, including microbes, bacteria, or fungi. In various applications, the structure 40 is a structure such as a wall, floor, table top, door, handle, cover, device, or any structure 40 having the surface 8 likely to come into contact with a human. The imprinted multi-layer structure 5 can form a wall paper or plastic wrap for structures 40.

In a useful embodiment of the imprinted multi-layer structure 5 having the bi-layer 7, the biocidal particles 60 include a silver component, have a sulfur or chlorine component, have a copper component, are a salt, are a silver sulfate salt, or are other biocidal particles 60. In an embodiment, the first or second cured layers 10, 20 include phosphors. The biocidal particles 60 can have a distribution of sizes so that some of the biocidal particles 60 are large particles, for example from two microns to 20 microns, and other particles are small particles, for example from 100 nm to two microns.

By biocidal layer is meant herein any layer that resists the growth of undesirable biological organisms, including microbes, bacteria, or fungi or more generally, eukaryotes, prokaryotes, or viruses. In particular, the biocidal bi-layer 7 inhibits the growth, reproduction, or life of infectious micro-organisms that cause illness or death in humans or animals and especially antibiotic-resistant strains of bacteria. The bi-layer 7 is rendered biocidal by including biocidal particles 60 such as ionic metals or metal salts in the first cured layer 10. Biocidal agents from the biocidal particles 60 can interact with any contaminants or biological organisms in the environment. The biocidal layer 7 or biocidal particle 60 is anti-microbial.

In other embodiments, the biocidal first cured layer 10 has a thickness that is less than at least one diameter of one or more of the biocidal particles 60, has a thickness that is less than a mean diameter of the biocidal particles 60, or has a thickness that is less than the median diameter of the biocidal particles 60. Alternatively, the biocidal particles 60 have at least one diameter between 0.05 and 25 microns. In yet another arrangement, the second cured layer 20 is greater than or equal to 0.5 microns thick and less than or equal to 20 microns thick.

In yet another embodiment, the first or second cured layers 10, 20, have a hydrophobic surface, for example by providing a roughened surface either by imprinting or by a treatment such as sandblasting or exposure to energetic gases or plasmas.

Referring to FIGS. 2A to 2G and FIG. 4, a method of the present invention includes making the imprinted bi-layer 7 on the support 30 (FIG. 1) provided in step 100. A dispersion of biocidal particles 60 is formed in step 120, for example in a container 66 (FIG. 2A). The dispersion is coated over the support 30 to provide the first curable layer 13 in step 105 as shown in FIG. 2B. In an alternative embodiment, an uncured layer including biocidal particles 60 is laminated on the support 30 to provide the first curable layer 13.

In an embodiment, a dispersion of biocidal particles 60 is formed in a carrier such as a liquid, for example a curable resin, in the container 66 (FIG. 2A) in step 120 of FIG. 4. Making and coating liquids with dispersed particles is known in the art. A dispersion having biocidal particles 60 has been made. The dispersion included three-micron silver sulfate particles milled in an SU8 liquid to an average particle size of one micron, and successfully coated on glass and tested with *E. coli* and *S. aureus* bacteria.

In step 110 a second curable layer 23 is located over the first curable layer 13, for example by coating, as illustrated in FIG. 2C. In an alternative embodiment, the second curable layer 23 is made separately and laminated on or over the first curable layer 13 before the first curable layer 13 is cured.

The first curable layer 13 and the second curable layer 23 are formed in any of various ways, including extrusion or coating, for example spin coating, curtain coating, or hopper coating, or other methods known in the art. In other embodiments of the present invention, locating the first curable layer 13 includes laminating a first curable material on or over the support 30 or locating the second curable layer 23 includes laminating a second curable material on or over the first curable layer 13.

Referring to FIG. 2D, the first curable layer 13 and the second curable layer 23 are imprinted in a single step 125 with an imprinting stamp 90 having a structure with a structure depth 6 greater than the second layer thickness 26 of the second curable layer 23 (FIG. 2E) and then cured in a single step 130, for example with heat or radiation 92 to form the first cured layer 10 and the second cured layer 20 (FIG. 2F). The imprinting stamp 90 is removed in step 135 to form an imprinted bi-layer 7 with a topographical structure having a depth 6 greater than the second-layer thickness 26 of the second cured layer 20 (FIG. 2G) to form the bi-layer 7 of the imprinted multi-layer structure 5 of the present invention. Imprinting methods using stamps 90 are known in the art. In an optional step 140, a portion of the second cured layer 20 is removed, for example by etching or using energetic particles such as with plasma etching, reactive plasma etching, ion etching, or sandblasting the second cured layer 20. Such a removal treatment can remove a portion of any coating over the biocidal particles 60 to more readily expose the biocidal particles 60 to the environment. The removal can render the second cured layer 20 thinner or expose portions of the first cured layer 10 or biocidal particles 60 to the environment.

The imprinted multi-layer structure 5 having the structured bi-layer 7 of the present invention has been constructed in a method of the present invention using cross-linkable materials such as curable resins (for example using SU8 at suitable viscosities and PEDOT) coated on a glass surface and imprinted using a PDMS stamp to form micro-structures in the bi-layer 7.

Figure 2A:
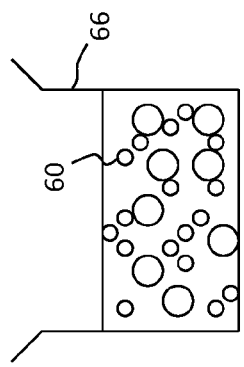
Figure 2B:
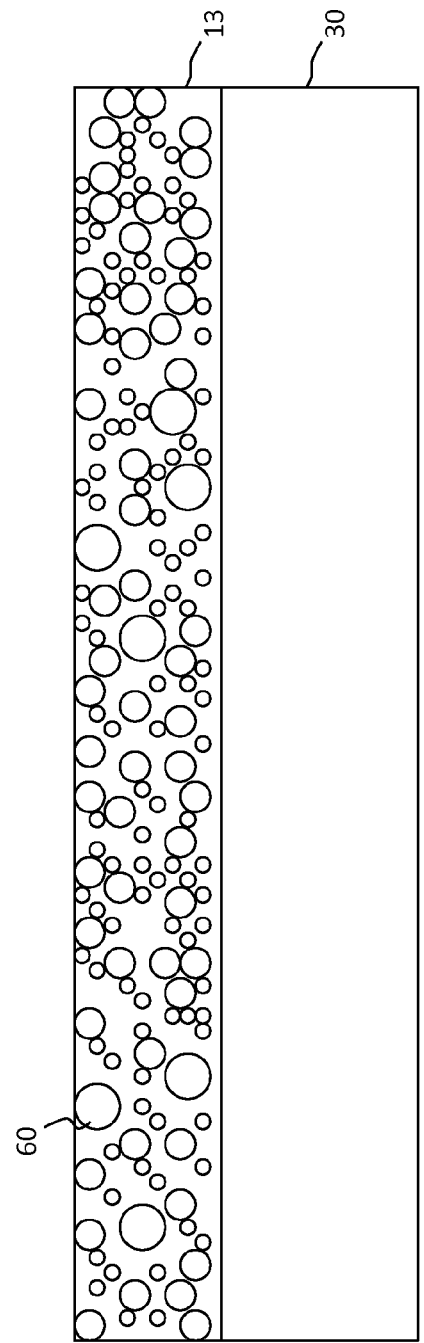
Figure 2C:
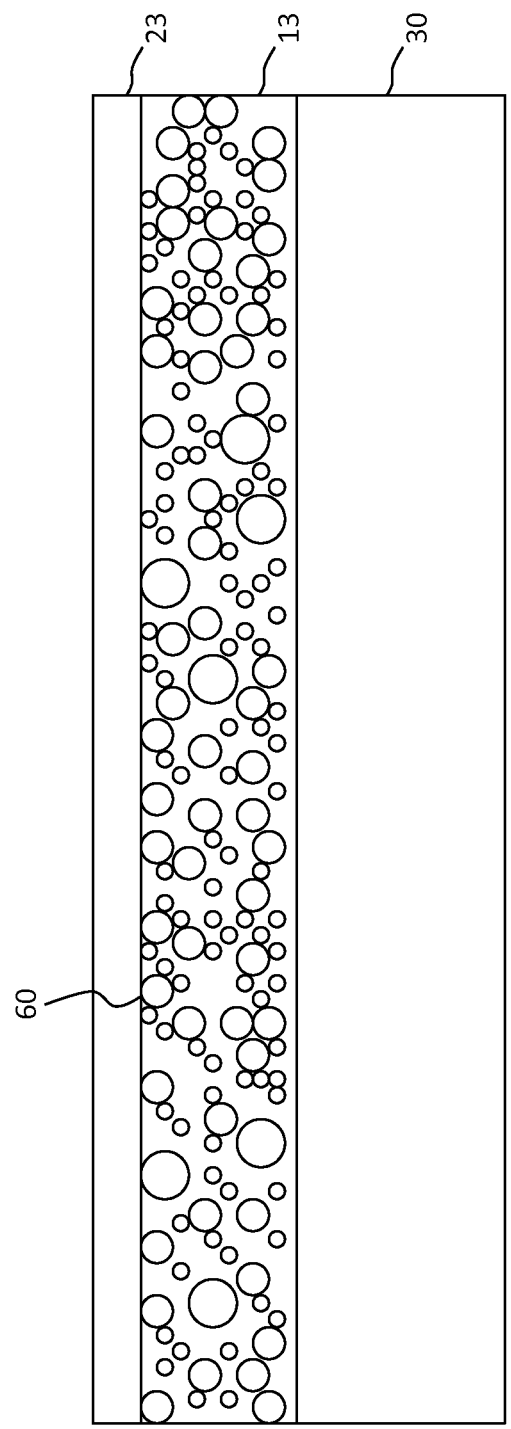
Figure 2D:
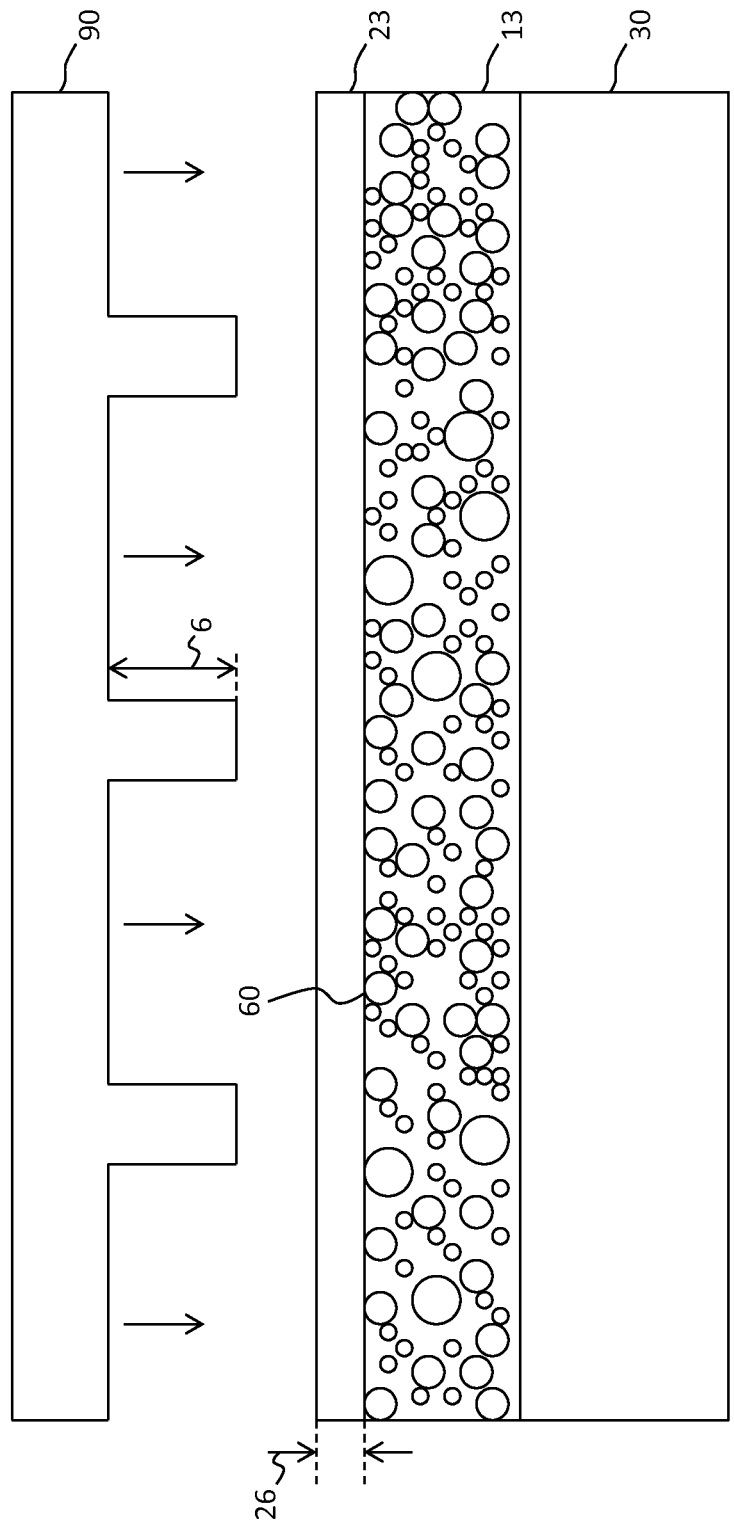
Figure 2E:
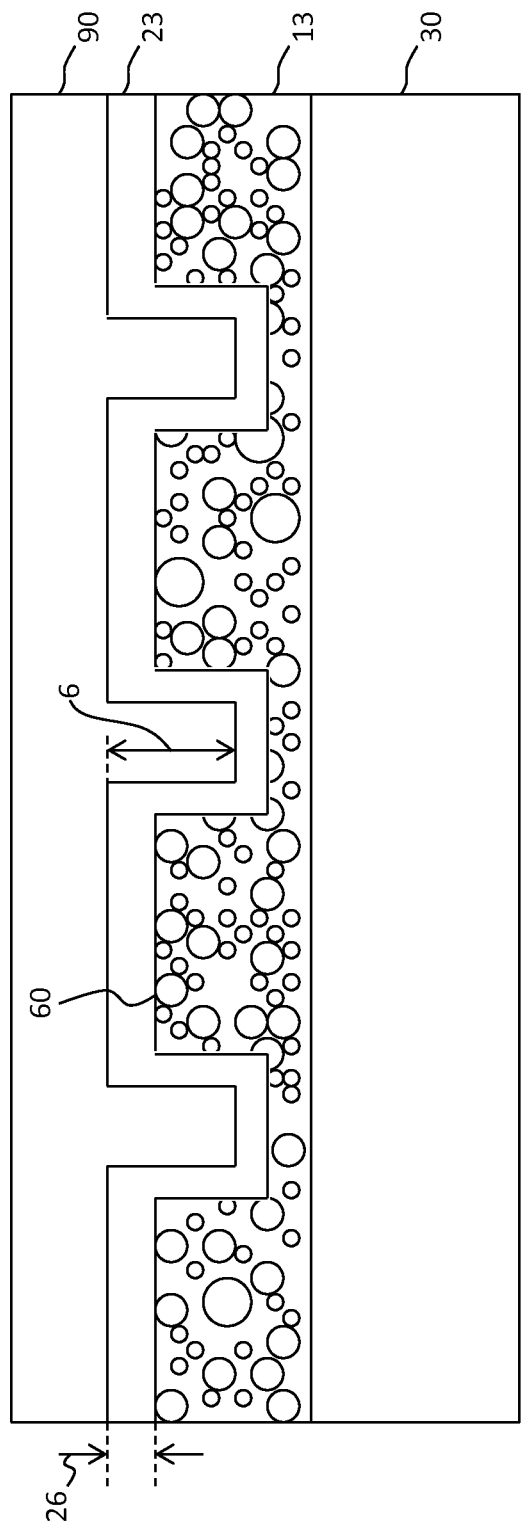
Figure 2G:
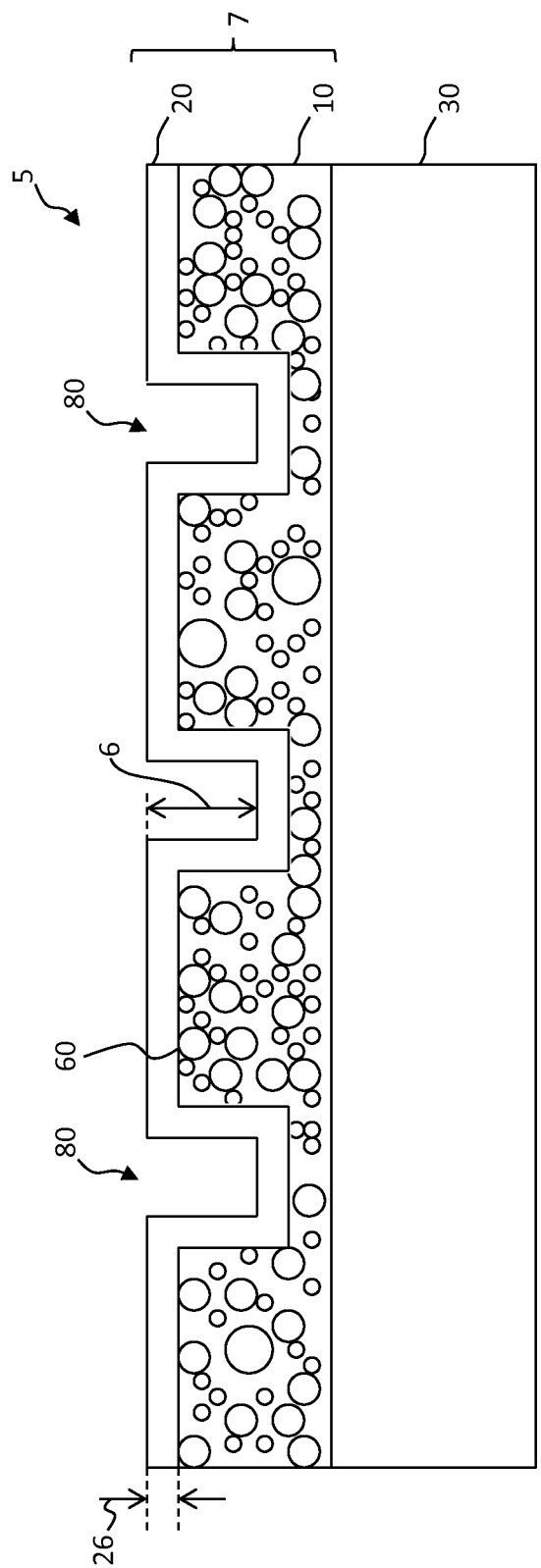
Figure 3:
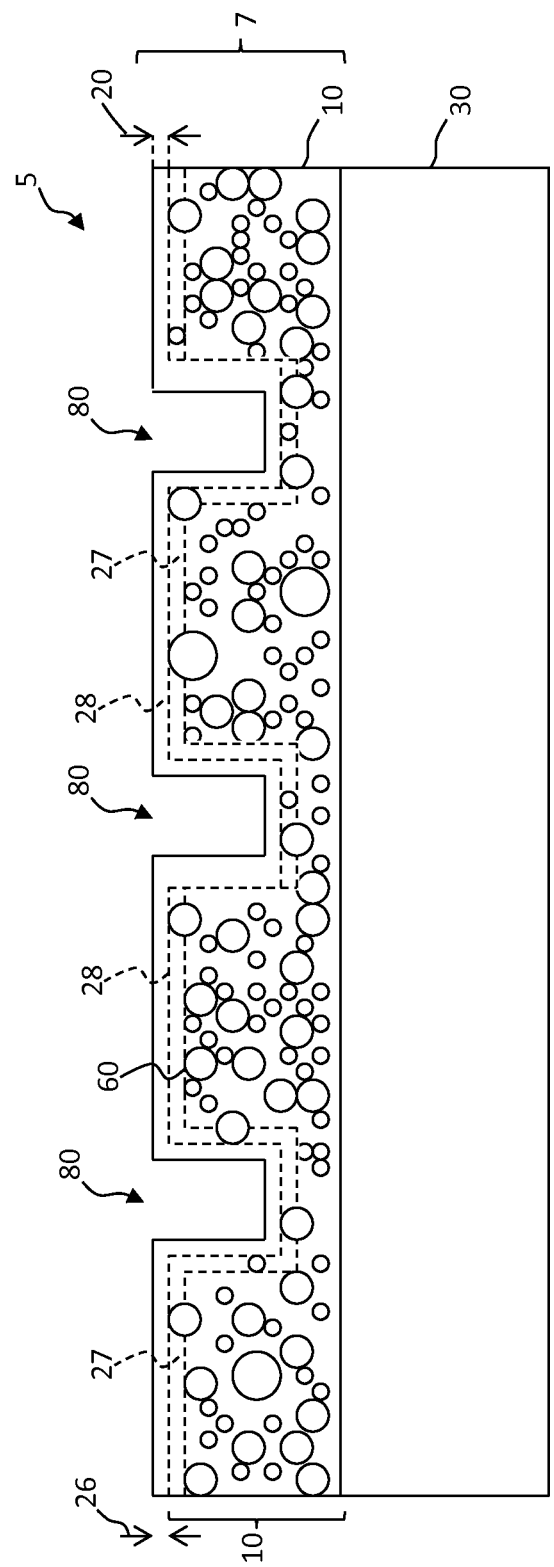
FIG. 3 is a cross section of an alternative embodiment of the present invention.

Referring to FIG. 3, the imprinting step 125 forming the indentations 80 of the multi-layer structure 5 (shown in FIGS. 2D and 2E) can result in the movement of some biocidal particles 60 into the original second curable layer 27 so that the second-layer thickness 26 is reduced as indicated with the dashed lines illustrating the final second-layer thickness 28. The second-layer thickness 26 is the portion of the second cured layer 20 between the biocidal particles 60 and the surface of the second cured layer 20 and can vary over the extent of the support 30.

Figure 4:
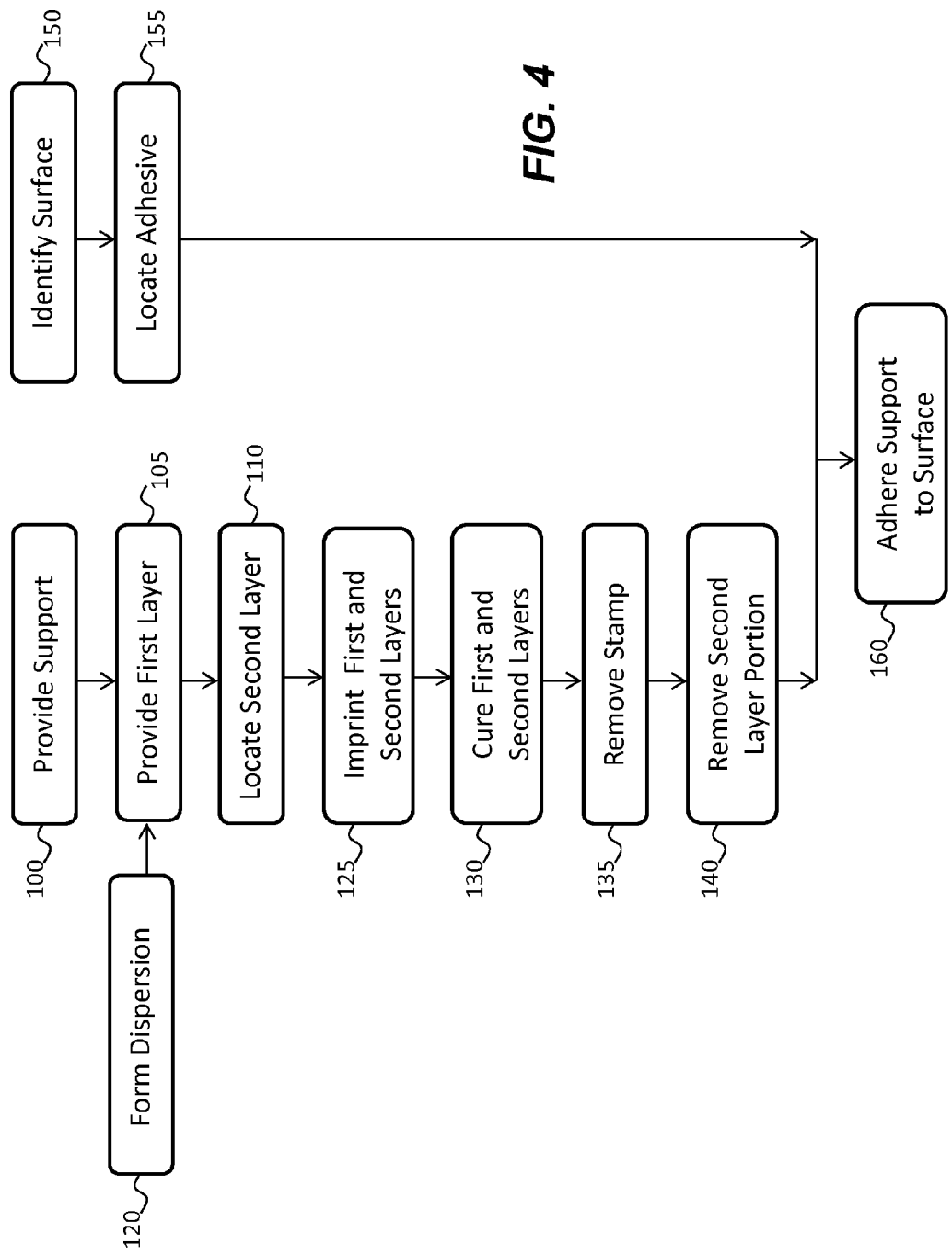
FIGS. 4 and 5 are flow diagrams illustrating methods of the present invention.

Referring further to FIG. 4 in an embodiment of the present invention, the surface 8 of the structure 40 is identified in step 150. The surface 8 is a surface which it is desired to keep free of microbes, for example a wall, floor, table top, door, handle, knob, cover, or device surface, especially any surface 8 found in any type of medical institution. In an embodiment, the surface 8 is planar; in another embodiment, the surface 8 is non-planar. In step 155, an adhesive is located, for example on the surface 8 or on the side of the support 30 opposite the first cured layer 10, to form the adhesive layer 50. The support 30 is adhered to the surface 8 in step 160. In a further embodiment, the support 30, first cured layer 10, and second cured layer 20 are heated to shrink the imprinted multi-layer structure 5 on the surface 8 if the surface 8 is non-planar. In an embodiment, the heating step (not shown separately) is also the adhesion step 160 and a separate adhesive layer 50 is not necessary or used. In an embodiment, the second cured layer 20 is thinner than the first cured layer 10.

In an embodiment, the first cured layer 10 includes a first cross-linkable material, the second cured layer 20 includes a second cross-linkable material and the curing step 130 cross-links the first cross-linkable material to the second cross-linkable material. In another embodiment, the first material includes a first cross-linkable material and the second material includes a second cross-linkable material that is different from the first cross-linkable material and the curing step 130 cross-links the first cross-linkable material to the second cross-linkable material. Alternatively, the first material includes a first cross-linkable material, the second material includes a second cross-linkable material that is the same as the first cross-linkable material, and a third material is included in either the first material or the second material but not both the first and second materials and the curing step 130 cross-links the first cross-linkable material to the second cross-linkable material.

Figure 5:
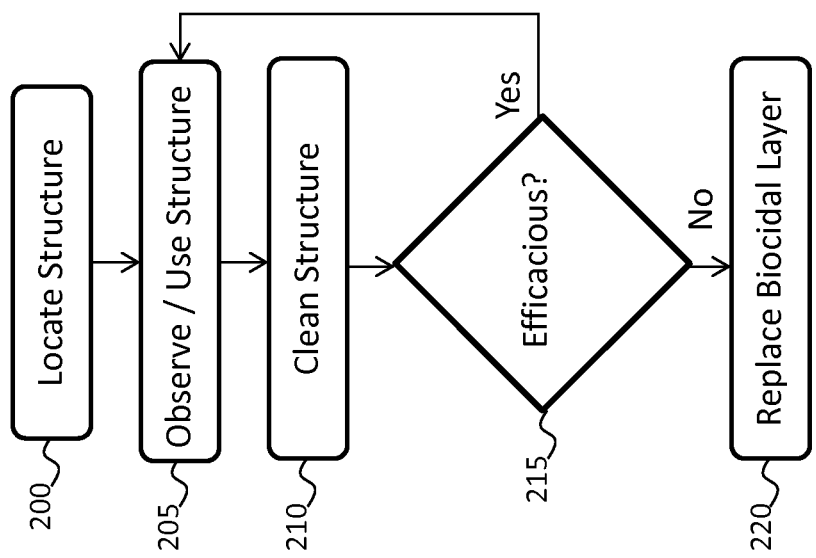

Referring to FIG. 5, in various embodiment of the present invention, the biocidal bi-layer 7 is located on the surface 8 in step 200 and observed or used over time in step 205. Periodically or as needed, the imprinted multi-layer structure 5 is cleaned in step 210, for example by washing with water or with a cleaning fluid, or wiping the multi-layer structure 5. The imprinted multi-layer structure 5 is repeatedly observed or used (step 205) and cleaned (step 210) until it is no longer efficacious for its intended purpose. If the biocidal imprinted multi-layer structure 5 is determined (step 215) not to be efficacious, it is replaced, removed, or covered over in step 220.

In an embodiment, the cleaning step removes dead micro-organisms or dirt from the surface of the bi-layer 7 so that the biocidal efficacy of the biocidal particles 60 is improved in the absence of the dead micro-organisms or dirt. Useful cleaners include hydrogen peroxide, for example 2% hydrogen peroxide, water, soap in water, or a citrus-based cleaner. In an embodiment, the 2% hydrogen peroxide solution is reactive to make oxygen radicals that improve the efficacy of biocidal particles 60. In various embodiments, cleaning is accomplished by spraying the surface of the bi-layer 7 with a cleaner and then wiping or rubbing the surface. The cleaner can dissolve the second cured layer 20 material (e.g. cross linking material) and the wiping or rubbing can remove dissolved material or abrade the surface of the second cured layer 20 to expose other biocidal particles 60 or increase the exposed surface area of exposed biocidal particles 60.

Alternatively, the cleaning or washing step 210 refreshes the biocidal particles 60, for example by a chemical process, to improve their biocidal efficacy. This can be done, for example, by ionizing the biocidal particles 60, by removing oxidation layers on the biocidal particles 60, or by removing extraneous materials such as dust from the biocidal particles 60.

Replacement of the bi-layer 7 can proceed in a variety of ways. In one embodiment, another biocidal imprinted multi-layer structure 5 is simply located over the biocidal imprinted multi-layer structure 5. Thus, the biocidal multi-layer structure 5 becomes the structure 40 and another biocidal imprinted multi-layer structure 5 is applied to the structure 40, for example with the adhesive layer 50 (FIG. 1). In another embodiment, the biocidal imprinted multi-layer structure 5 is removed and another biocidal imprinted multi-layer structure 5 put in its place. As shown in FIG. 1, the support 30 is adhered to the structure 40 with the adhesive layer 50. Chemical, mechanical, or heat treatments are applied to the biocidal multi-layer structure 5 to loosen, dissolve, or remove the adhesive layer 50 so the biocidal imprinted multi-layer structure 5 can be removed and another adhesive layer 50 applied to the structure 40 to adhere the biocidal imprinted multi-layer structure 5 to the structure 40. In an embodiment, the biocidal imprinted multi-layer structure 5 is mechanically peeled from the structure 40 and another biocidal imprinted multi-layer structure 5 having the adhesive layer 50 is adhered to the structure 40.

In another embodiment of the present invention, fluorescent or phosphorescent materials are included in the first cured layer 10 and are illuminated. The fluorescent or phosphorescent materials respond to ultra-violet, visible, or infrared illumination and emit light that can be seen or detected and compared to a threshold emission value. Thus, the continuing presence of the first cured layer 10 is observed. When light emission in response to illumination is no longer present at a desired level, the first cured layer 10 is replaced.

The present invention is useful in a wide variety of environments and on a wide variety of surfaces 8, particularly surfaces 8 that are frequently handled by humans. The present invention can reduce the microbial load in an environment and is especially useful in medical facilities.

The invention has been described in detail with particular reference to certain embodiments thereof, but it will be understood that variations and modifications can be effected within the spirit and scope of the invention.

PARTS LIST

- 5 multi-layer structure
- 6 depth
- 7 bi-layer
- 8 surface
- 10 biocidal first cured layer
- 13 first curable layer
- 16 first-layer thickness
- 20 second layer/second cured layer
- 23 second curable layer
- 26 second-layer thickness
- 27 original second-layer thickness
- 28 final second-layer thickness
- 30 support
- 36 support thickness
- 40 structure
- 50 adhesive layer
- 60 biocidal particle
- 66 container
- 80 indentations
- 90 stamp
- 92 radiation
- 100 provide support step
- 105 locate first layer step
- 110 locate second layer step
- 120 form dispersion step
- 125 imprint first and second layers step
- 130 cure first and second layers step
- 135 remove stamp step
- 140 remove second layer portion step
- 150 identify surface step
- 155 locate adhesive step
- 160 adhere support to surface step
- 200 locate structure step
- 205 observe/use structure step
- 210 clean structure step
- 215 determination step
- 220 replace biocidal layer step

The invention claimed is:

1. A method of making a multi-layer biocidal structure, comprising:
    providing a support;
    providing a first curable layer on the support, the first curable layer including dispersed multiple biocidal particles;
    providing a second curable layer on the first curable layer, wherein multiple biocidal particles are dispersed within only the first curable layer;
    imprinting the first curable layer and the second curable layer in a single step with an imprinting stamp having a structure that forms microscopic indentations in the first curable layer and the second curable layer corresponding to a magnitude of the indentations having a depth greater than the thickness of the second curable layer;
    curing the first curable layer and the second curable layer in a single step to form a first cured layer and a second cured layer; and
    removing the imprinting stamp.

2. The method of claim 1, wherein the first curable layer includes a first cross-linkable material, the second curable layer includes a second cross-linkable material, and the step of curing cross links the first cross-linkable material to the second cross-linkable material.

3. The method of claim 2, wherein the first cross-linkable material is the same material as the second cross-linkable material.

4. The method of claim 1, wherein providing the first curable layer includes coating or laminating a first curable material on or over the support.

5. The method of claim 1, wherein providing the second curable layer includes coating or laminating a second curable material on or over the first curable layer.

6. The method of claim 1, further including forming a dispersion of biocidal particles in a first curable material and then providing the first curable material on or over the support to form the first curable layer.

7. The method of claim 1, wherein the second curable layer is thinner than the first curable layer.

8. The method of claim 1, wherein the second curable layer is thinner than a mean or median diameter of the particles.

9. The method of claim 1, wherein the second curable layer is thicker than a mean or median diameter of the particles.

10. The method of claim 1, wherein the first cured layer has a different color than the second cured layer.

11. The method of claim 1, wherein the depth of the indentations is between 0.5 microns and 50 microns.

12. The method of claim 1, wherein the depth of the indentations is between 0.5 microns and 10 microns.

13. The method of claim 1, wherein the depth of the indentations is between 0.5 microns and 5 microns.

14. The method of claim 1, wherein the depth of the indentations is between 0.5 microns to 2 microns.

* * * * *